April 18, 1950 F. MEILLAND Plant Pat. 934
ROSE PLANT
Filed Oct. 6, 1948
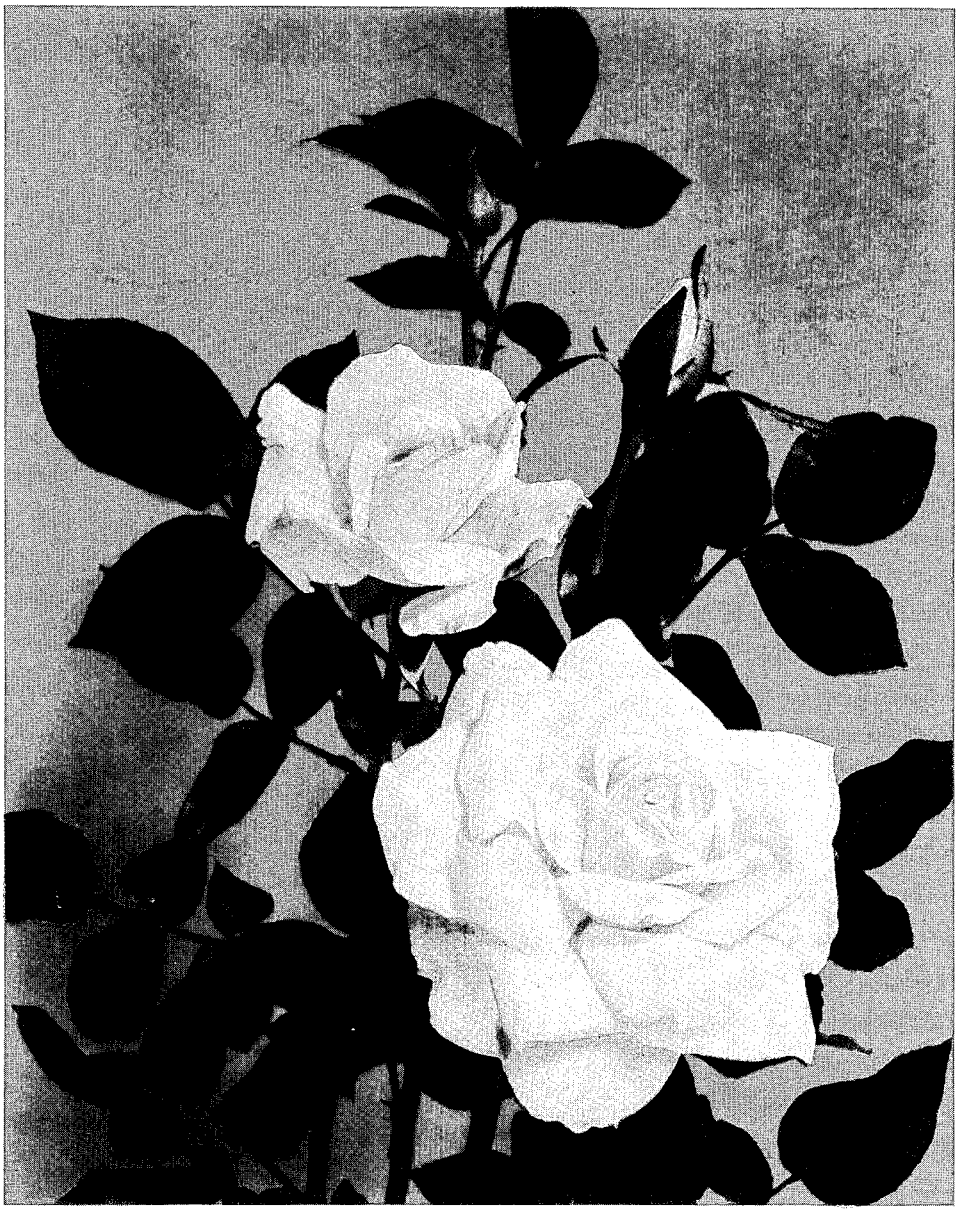
Inventor
F. Meilland
By Robb & Robb
Attorneys Patented Apr. 18, 1950

Plant Pat. 934

UNITED STATES PATENT OFFICE

934

ROSE PLANT

Francis Meilland, Cap Azura, Cap D'Antibes, France, assignor to The Conard-Pyle Company, West Grove, Pa., a corporation of Pennsylvania Application October 6, 1948, Serial No. 53,012

1 Claim. (Cl. 47—61)

The present invention relates to a new and distinct variety of rose plant having, in addition to excellent qualities of growth, floriferousness, vigor and disease resistance, most unusual color characteristics of beauty in the flower, in that the blooms reverse the usual color sequence of fading from dark to light, i. e. as the bud unfolds, the parts of the petals first exposed to light gradually turn to interesting configurations or shadings of light pink or light pink to darker, even carmine, shades, while the part of the petal unexposed to the sunshine remains a lighter shade—thus on one surface creating a light and shading contrast.

In the drawing are shown specimens of this new variety, illustrating the flowers at different stages of development from bud to full blown blossoms.

The following is a detailed description of the new variety, all reference to color being in accordance with Ridgway's Color Standards and Nomenclature and ordinary dictionary definition.

Type: Hardy; bush; outdoor; seedling; for cut flowers and garden decoration.
Class: Hybrid tea.
Propagation: Holds its distinguishing characteristics through succeeding propagations by budding.
Parentage: Peace×(Signora×Mrs. John Laing).

*Flower*

Locality where grown: West Grove, Pennsylvania.
Flowers borne: Singly or occasionally two to stem; on very strong, long stems.
Quantity of bloom: Free; outdoors.
Continuity: Continuous.
Fragrance: Penetrating; damask rose.
Bud:

*Peduncle.*—Medium length; heavy; erect; medium rough; numerous brown minute prickles. Color—Yellowish Oil Green, Plate V.

*Before calyx breaks.* — Size — medium. Form—pointed; with foliaceous appendages on the surface of the bud; with slender, cut foliaceous parts extending beyond the tip of the bud equal to ¼ or more of its length.

*As calyx breaks.*—Color—Pale Green Yellow, Plate V, shading to Pompeian Red, Plate XIII.

*As first petal opens.* — Size — medium. Form—ovoid. Color—outside: shading from Buff Yellow, Plate IV, to Bittersweet Pink, Plate II, to Rose Color, Plate XII, with tinges of Spinel Red, Plate XXVI; inside: shading from Buff Yellow, Plate IV, at base to Bittersweet Pink, Plate II, to Chatenay Pink, Plate XIII, to Rose Color, Plate XII, at very apex.

*Opening.*—Opens up well.

Bloom: Size, when fully open—large; 3¾" to 4¼".

*Petalage.*—Very double; from 55 to 90 petals; most arranged regularly, a few irregularly.

*Form.*—High center at first, remaining high centered (decorative form); petals remaining at first tightly cupped with petal edges slightly rolled outward; becoming later, at maturity, tightly cupped with petal edges loosely rolled outward.

Petals: Thick; soft; with inside satiny and outside satiny.

*Shape.*—Outside—obovate. Intermediate—obovate. Inside—oval to obovate.

*Color.*—Colors are modified by being washed and tinted with other colors.

This description of a newly opened flower was made from a rose grown outdoors in the month of August at West Grove, Pennsylvania:

*Color. — Outside petal* — outside surface: shading from Pinard Yellow, Plate IV, at the base to pale Seashell Pink, Plate XIV, to Rose Pink, Plate XII, and frequently to Rose Color, Plate XII, at outer edge; inside surface: shading from Lemon Chrome, Plate IV, at base to Ivory Yellow, Plate XXX, to Deep Rose Pink, Plate XII, and sometimes to Rose Color, Plate XII, at edge. *Intermediate petal*—outside surface: shading from Martius Yellow, Plate IV, at base to Flesh Color, Plate XIV, to Rose Pink, Plate XII, with a tinge of Tyrian Rose, Plate XII, at apex; inside surface: shading from Empire Yellow, Plate IV, at the base to Capucine Buff, Plate III, to Pale Salmon Color, Plate XIV, occasionally with a tinge of Tyrian Rose, Plate XII, at apex. *Inner petal*—outside surface: shading from Picric Yellow, Plate IV, at the base to Begonia Rose, Plate I, to Orient Pink, Plate II, at apex; inside surface: shading from Pinard Yellow, Plate IV, at the base to Capucine Buff, Plate III, over most of the petal.

This description was made from a rose that was open for three days outdoors in the month of August at West Grove, Pennsylvania:

*Color.—Outside petal*—outside surface: shading from Martius Yellow, Plate IV, at the base to white to Rose Pink, Plate XII, to Pale Rosolane Purple, Plate XXVI, at outer edge; inside surface: shading from Pinard Yellow, Plate IV, at the base to white to Cameo Pink, Plate XXVI, with streaks of Pale Rosolane Purple, Plate XXVI. *Inside petal*—outside surface: Capucine Buff, Plate III, shaded with Flesh Color, Plate XIV; inside surface: Capucine Buff, Plate III, with white area at apex.

*General color effect.*—Newly opened flower—shading from light Shrimp Pink, Plate I, to Hermosa Pink, Plate I, tinged with Tyrian Pink, Plate XII. Three days open—shading from light Rosolane Purple, Plate XXVI, to Pale Rosolane Purple, Plate XXVI, at outer edge to light Shell Pink, Plate XXVIII, over most of the flower to Flesh Color, Plate XIV, at the very center.

*Reproductive organs*

Stamens: Medium number; arranged regularly about pistils, occasionally an anther fused with petaloid.

Filaments: medium length; most with anthers. Color—Japan Rose, Plate XXVIII.

Anthers: Medium size; all open at once, occasionally an anther fused with a pistil. Color—Light Cadmium, Plate IV, with Pinard Yellow, Plate IV, center stripe.

Pollen: Moderate amount, Cadmium Yellow, Plate III.

Pistils: Medium number.

Styles: Uneven, medium length; medium heavy; bunched.

Stigma: Light Orange Pink, Plate II, to Light Salmon Orange, Plate II.

Ovaries: All enclosed in calyx.

Hips: Very short; Lettuce Green, Plate V, walls medium thin.

Sepals: Permanent; medium length; spear-shaped.

Seeds: Very few; small.

*Plant*

Foliage:

*Leaves.*—Compound of three or five leaflets; abundant; moderately large; leathery.

*Leaflets.*—Oval with apex acute; base round, occasionally slightly oblique; margin simply serrate.

*Color.—Mature*—upper surface: Dark Cedar Green, Plate VI; under surface: Light Cress Green, Plate XXI. *Young*—upper surface: Maroon, Plate I; under surface: Mineral Red, Plate XXVII.

*Rachis.* — Medium heavy. Upper side: grooved; under side: sparsely hairy.

*Stipules.*—Moderately long; medium width; medium length points turning out at angle of less than 90°. Occasionally stipules have a marked uneven length of attachment to rachis.

*Disease.*—Resistant to mildew and blackspot.

Growth:

*Habit.*—Upright; little branched.

*Growth.*—Vigorous

*Canes.*—Heavy.

*Main Stems.*—Gray-green. Thorns — few; short; hooked downward; with long, broad base. *Prickles* and *Hairs*—none.

*Branches.*—Gray-green; some branches with a faint reddish tinge. *Thorns* — rare; hooked downward; short; narrow base. *Prickles*—none. *Hairs*—few; gray.

*New shoots.*—Lettuce Green, Plate V, shaded with Cameo Brown, Plate XXVIII. *Thorns*—few; medium length; hooked downward with long, narrow base. *Prickles*—none. *Hairs*—very few; gray.

I claim:

A new and distinct variety of rose plant characterized as to novelty by its combination with excellent habits of vigorous growth, fluoriferousness, and disease resistance, of unique color characteristics in the flowers in respect of the sequence of contrasting shadings on the petal surface, substantially as shown and described.

FRANCIS MEILLAND.

No references cited.